(12) United States Patent
Elmaloglou et al.

(10) Patent No.: US 10,676,421 B2
(45) Date of Patent: Jun. 9, 2020

(54) METHOD FOR PRODUCING (METH)ACRYLIC ESTERS

(71) Applicant: Arkema France, Colombes (FR)

(72) Inventors: Marianthi Elmaloglou, Metz (FR); Anne Moreliere, Longeville-Les-St-Avold (FR); Serge Tretjak, Roulhing (FR)

(73) Assignee: Arkema France, Colombes (FR)

( * ) Notice: Subject to any disclaimer, the term of this patent is extended or adjusted under 35 U.S.C. 154(b) by 86 days.

(21) Appl. No.: 16/081,060

(22) PCT Filed: Feb. 14, 2017

(86) PCT No.: PCT/FR2017/050331
§ 371 (c)(1),
(2) Date: Aug. 30, 2018

(87) PCT Pub. No.: WO2017/153653
PCT Pub. Date: Sep. 14, 2017

(65) Prior Publication Data
US 2019/0071384 A1 Mar. 7, 2019

(30) Foreign Application Priority Data
Mar. 10, 2016 (FR) ..................................... 16 52001

(51) Int. Cl.
C07C 67/08 (2006.01)
C07C 67/56 (2006.01)
(Continued)

(52) U.S. Cl.
CPC ............ *C07C 67/08* (2013.01); *B01D 71/027* (2013.01); *B01J 19/2475* (2013.01); *C07C 67/56* (2013.01); *C07C 69/54* (2013.01); *Y02P 20/582* (2015.11)

(58) Field of Classification Search
None
See application file for complete search history.

(56) References Cited

U.S. PATENT DOCUMENTS 6,107,515 A 8/2000 Yamaguchi et al.
9,908,838 B2 3/2018 Tretjak et al.
(Continued)

FOREIGN PATENT DOCUMENTS

CN 105170033 A 12/2015
FR 2980475 B1 8/2013

OTHER PUBLICATIONS

Chen et al. (CN 105170033) English Machine Translation (Year: 2015).*

(Continued)

*Primary Examiner* — Sudhakar Katakam
*Assistant Examiner* — Jennifer C Sawyer
(74) *Attorney, Agent, or Firm* — Lynn B. Morreale

(57) ABSTRACT

The subject of the present invention is a process for the synthesis of $C_1$-$C_{10}$ alkyl (meth)acrylates, by direct esterification of the (meth)acrylic acid by the corresponding alcohol, the reaction being carried out in a fixed bed membrane reactor under conditions in which the water generated by the reaction is eliminated from the reaction mixture as it is formed. The process according to the invention may operate under conditions for which the reagents are not in excess, thereby minimizing the size and energy of the equipment for separation/recycling of the streams generated during the purification of the reaction medium.

6 Claims, 3 Drawing Sheets

(51) Int. Cl.
*B01D 71/02* (2006.01)
*B01J 19/24* (2006.01)
*C07C 69/54* (2006.01)

(56) References Cited

U.S. PATENT DOCUMENTS

2016/0272570 A1* 9/2016 Tretjak .................... C07C 51/44
2016/0376217 A1   12/2016 Tretjak et al.

OTHER PUBLICATIONS

Truong HT et al. Separation and Purification Technology, vol. 120, 2013, pp. 24-34.
Emine Sert et al., in Chemical Engineering and Processing, vol. 81, 2014, pp. 41-47.

* cited by examiner a)

b)

METHOD FOR PRODUCING (METH)ACRYLIC ESTERS

CROSS-REFERENCE TO RELATED APPLICATIONS

This application is a national stage application under 35 U.S.C. § 371 of PCT/FR20171050331, filed Feb. 14, 2017 which claims benefit to application FR16.52001, filed Mar. 10, 2016.

FIELD OF THE INVENTION

The present invention relates to the production of (meth) acrylic esters, and the subject is more particularly a process for the synthesis of $C_1$-$C_{10}$ alkyl (meth)acrylates, by direct esterification of the (meth)acrylic acid by the corresponding alcohol, the reaction being carried out in a membrane reactor under conditions in which the water generated by the reaction is eliminated from the reaction mixture as it is formed.

Technical Background and Technical Problem

It is known practice to produce (meth)acrylic esters from an esterification reaction between an alcohol and a (meth) acrylic acid. This reaction is an equilibrated catalyzed reaction with generation of water. It is also accompanied by side reactions producing impurities.

It is necessary to eliminate the water produced in order to shift the equilibrium, and it is necessary to recycle unreacted reagents (alcohol and acid) and also to eliminate impurities, in particular lighter compounds than the ester and heavier compounds than the ester, so as to obtain a product which meets commercial specifications.

To this end, a set of treatments of the reaction mixture is generally carried out, by means of distillations and/or extractions, or settling out operations, which set of treatments is both relatively complex to carry out, especially due to the presence of azeotropic mixtures, and costly in terms of energy.

The reaction mixture contains the desired ester, water, unreacted acid and alcohol, "light" by-products having a boiling point lower than that of the ester, and "heavy" by-products, that is to say having a boiling point higher than that of the ester. The purification sequence applied to the reaction mixture generates various streams, the composition of which varies depending on the apolar nature of the alcohol and of the ester, that is to say according to the length of the alkyl chain of the alcohol used.

These streams have the common feature of containing water resulting from the reaction and/or from the extraction steps, which contributes to the complexity of the treatment for purification of the desired ester.

In the process for producing (meth)acrylic ester described in patent application FR 2 980 475 in the applicant's name, or in the publication by Truong H T et al. *Separation and Purification Technology*, vol. 120, 2013, pp 24-34, using modules for dehydration by membrane separation is proposed to dehydrate streams comprising (meth)acrylic ester and unreacted alcohol with a view to effectively eliminating water and to lead to good selectivity for (meth)acrylic ester.

These dehydration modules may be employed at various places in the installation, for example at the end of the reaction step or at the recycling of the stream comprising unreacted alcohol for a well-defined concentration range of the various compounds. In particular, a dehydration step may be carried out on an intermediate reaction stream resulting from a first stage of the reaction and supplying a second reactor in which a second stage of the reaction is conducted. Dehydration by membrane separation may also be carried out directly in the reactor, by means of an immersed module equipped with tubes fitted with ceramic membranes, with extraction of the water inside the tubes.

Avoiding the formation of a loop of water which is harmful to the productivity and energy consumption of a process for producing $C_4$-$C_{10}$ alkyl (meth)acrylates, by applying a step of dehydration by membrane separation to streams intended to be purified and/or recycled, was also proposed in document WO 2015/086978. These streams are, especially, the aqueous stream originating from the settling out of the reaction mixture, the stream subjected to the final distillation leading to the recovery of the purified (meth) acrylic ester, or the stream resulting from the distillation of the light by-products present in the reaction mixture.

Moreover, the process described in document WO 2015/063388 makes it possible to significantly reduce the formation of heavy by-products and thus to improve the productivity of a process for synthesizing methyl or ethyl (meth) acrylate, by minimizing the amount of water introduced into the reactor. The water introduced may originate from the alcohol supply or from the recycling of the aqueous stream comprising the unreacted acid and/or the unreacted alcohol. A step of dehydration by membrane separation, by distillation or by pressure swing adsorption is applied to at least one of the streams supplying the reactor.

Despite the various improvements described in the prior art, there remains a need to provide a process for producing acrylic and methacrylic esters which enables effective elimination of water in order to shift the equilibrium of the reaction and reduce the energy cost associated with the purification treatment, and which has good selectivity and improved productivity.

Eliminating the water formed in the reactor by placing a pervaporation membrane in the bottom portion of the reactor, making it possible to separate the water and/or alcohol from the reaction medium by means of a vacuum pump, has already been proposed in the process for synthesizing (meth) acrylic esters from (meth)acrolein and alcohol in the presence of air described in U.S. Pat. No. 6,107,515. In a preferred configuration, the water is extracted from the reaction medium through an inorganic membrane of zeolite type in a medium kept at neutral pH. The surface are of the membrane used is limited by the size of the reactor bottom. This configuration also does not enable intimate and direct contact between the catalyst, in contact with which the reaction occurs, and the membrane, since this catalyst is kept in the liquid phase by stirring of the reaction mixture.

Similarly, Emine Sert et al., in *Chemical Engineering and Processing*, vol. 81, 2014, pp 41-47, describe a batch process for producing butyl acrylate by stirring/fluidization of the catalyst in a reactor containing a membrane at the bottom thereof. This process has water elimination performance properties linked to the limited size of the surface of the membrane which can be used.

Patent application CN 105170033 describes an annular circulating bed reactor technology and the use thereof for carrying out esterification reactions while continuously eliminating the water generated by the reaction. This technology makes it possible to obtain higher conversions than those of a conventional fixed-bed reactor, but has the drawback of being complex to employ. The ceramic membrane used operates according to a process of pressure-gradient nanofiltration, and has a large porosity which limits the separation selectivity.

The academic literature has already described esterification/dehydration by pervaporation pairings for different acids such as acetic acid, lactic acid, succinic acid, propionic acid, tartaric acid or oleic acid. These systems are essentially based on the use of a module for dehydration by pervaporation placed on a loop for recirculating the reaction stream linked to the reaction portion. Membranes from various suppliers have been used in these processes; mention may be made of the Pervape 1005, GFT® 1005, Pervap® 2201, zeolite T, or HybSi®-type silica membranes.

Unlike acetates or lactates, (meth)acrylates are highly reactive molecules due to the presence of a double bond, and are liable to form polymers and hence foul membranes. It is therefore necessary to adapt the operating conditions in order that these monomers do not polymerize either at the surface of the membrane or in the porous structure during separation.

The inventors have now discovered that by using a membrane reactor comprising a separation membrane and an esterification catalyst in an acid medium, it is possible to conduct the esterification reaction while eliminating the water generated by the reaction as it is formed, without fouling of the membrane being observed.

The invention thus provides a process for synthesizing (meth)acrylic esters having improved productivity and selectivity, and able to operate under conditions for which the reagents are not in excess, thereby minimizing the size and energy of the equipment for separation/recycling of the streams generated during the purification of the reaction medium.

SUMMARY OF THE INVENTION

The subject of the present invention is a process for producing an alkyl (meth)acrylate by direct esterification of the (meth)acrylic acid with a linear or branched alcohol comprising from 1 to 10 carbon atoms, in the presence of an esterification catalyst, characterized in that it employs a fixed bed membrane reactor in which the esterification reaction is conducted, while eliminating the water generated by the reaction as it is formed.

According to the invention, "membrane reactor" is intended to mean a membrane module for dehydration, coupled to a heterogeneous esterification catalyst.

According to one embodiment, the esterification catalyst is deposited at the surface of a membrane module for dehydration.

According to one embodiment, the esterification catalyst is deposited within a membrane module for dehydration, for example in the form of a tube.

According to one embodiment, the esterification catalyst is a heterogeneous acid catalyst.

According to one embodiment, the membrane dehydration is a dehydration by pervaporation or by vapour permeation.

According to one embodiment, the membrane module comprises a hydrophilic type membrane, either polymeric or hybrid (polymer membrane deposited on an inorganic support), or an inorganic type membrane, for example based on modified silica or ceramic.

According to one embodiment, the process is chosen from the processes of continuous, semi-continuous, or batch type.

The process is preferably continuous.

DETAILED DESCRIPTION OF THE INVENTION

Figure 1:
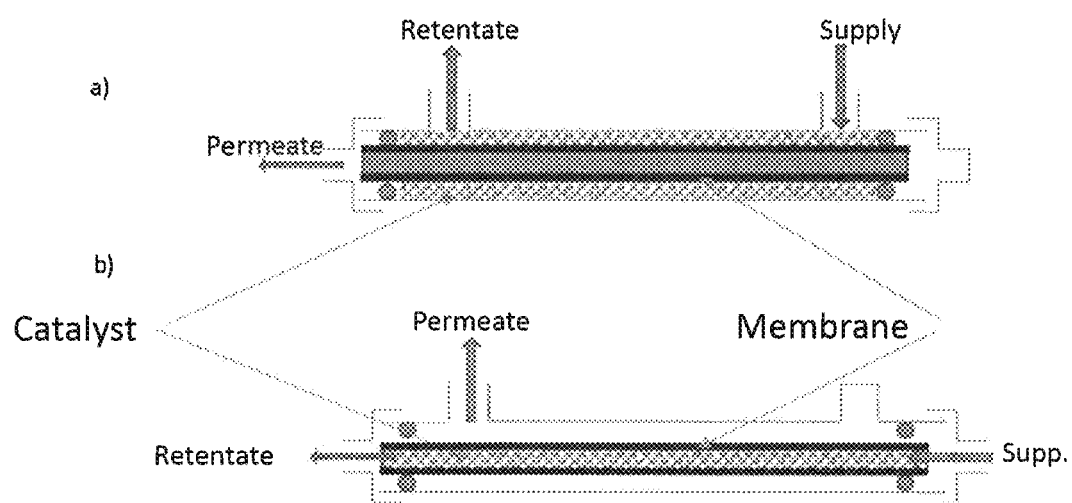
FIG. 1 schematically represents two examples of a membrane module for dehydration coupled to a heterogeneous esterification catalyst.

The invention is now described in greater detail and nonlimitingly in the description which follows.

The terms "(meth)acrylic" and "(meth)acrylate" mean, as is customary, "acrylic or methacrylic" and "acrylate or methacrylate", respectively.

The alcohol used in the context of the invention may be linear or branched. It may be a primary alcohol or a secondary alcohol. It may comprise from 1 to 10 carbon atoms. It may be substituted or unsubstituted, and preferably it is unsubstituted. The alcohol may especially be methanol, ethanol, butanol, 2-ethylhexanol or 2-octanol. The alcohol is preferably ethanol.

The corresponding esters obtained are methyl acrylate or methyl methacrylate, ethyl acrylate or ethyl methacrylate, butyl acrylate or butyl methacrylate, 2-ethylhexyl acrylate or 2-ethylhexyl methacrylate, 2-octyl acrylate or 2-octyl methacrylate.

The (meth)acrylic acid is preferably acrylic acid.

The ester is preferably ethyl acrylate.

The reaction for esterification of the (meth)acrylic acid by the alcohol requires the presence of an esterification catalyst which is, according to the invention, a heterogeneous catalyst of solid type such as, for example, an acid cation exchange resin.

As examples of acid cation exchange resins, mention may be made of the range of Amberlyst® macroporous or gel resins from Dow, for example Amberlyst® 15 or 131, the Lewatit® range from Lanxess, for example Lewatite K1461 or the Diaion® range from MCC or Dowex® A.

The catalyst is generally in the form of grains of a size ranging from 300 to 800 microns.

According to the invention, the esterification reaction is conducted in a fixed-bed membrane reactor comprising a membrane module for dehydration coupled to the heterogeneous esterification catalyst. In this reactor, the water generated by the esterification reaction may be separated from the reaction medium as it is formed by means of the membrane module for dehydration.

The membrane module for dehydration may be a pervaporation unit (feedstock in liquid phase and vaporization of the aqueous permeate on passing through the membrane), or a vapour permeation unit (feedstock in vapour phase).

The membrane module for dehydration is preferably a unit for separation by pervaporation, that is to say with selective evaporation of the water through a membrane. The stream of water to be evaporated is characterized by a chemical potential difference on the two sides of the membrane module. This concentration gradient is maximized by raising the temperature and by applying a light pressure on the permeate (or vapour permeate) side. It is possible to obtain, according to this method, a permeate of high purity, greater than 95%, favouring the treatment or elimination thereof, and minimizing the loss of organic compounds of which use can be made by recycling into the process.

The membranes may be hydrophilic, of either polymeric or hybrid type (polymer membrane deposited on an inorganic support). Use may be made, for example, of the Pervap® 1005, Pervap® 1201 or Pervap® 4101 resins sold by Sulzer.

As an alternative, the membranes may be inorganic in order to favour strength in acid medium. It is possible to use a ceramic membrane or a membrane based on modified silica, for example of HybSi® type sold by Céramiques Techniques et Industrielles (CTI).

The membranes are selected due to their performance in terms of separation selectivity (water purity of the permeate) and of the flow rate of permeate passing through the membrane. It has been observed that inorganic membranes based on modified silica not only have good strength in an acrylic acid/acrylic ester medium, but also lead to a very water-rich permeate (water content of greater than 88%) comprising less than 1% ester, with stream flow rates much greater than those generally achieved with membranes of polymer type.

According to a preferred embodiment of the invention, the membrane reactor comprises a membrane module for dehydration by pervaporation based on modified silica, leading to increased productivity for the process according to the invention.

According to one configuration of the invention, the membrane reactor comprises a membrane module for dehydration, at the surface of which the esterification catalyst is located. The module may be planar or tubular.

According to another preferred configuration of the invention, the membrane reactor comprises a tubular membrane module for dehydration, within which an esterification catalyst is located.

The membrane reactor is preferably of multitubular type.

The membrane reactor is coupled to a vacuum pump in order to extract the water from the reaction medium. A vacuum compatible with industrial vacuums is used, generally of less than 100 mbar, for example of between 20 and 50 mbar.

The water leaving the membrane reactor is condensed and may be sent into one of the purification columns in order to recycle any traces of organic compounds which might have crossed the membrane. As an alternative, the condensed water is sent to the biological plant for treatment of the residual organic compounds.

The membrane reactor operates at a temperature ranging from 50° C. to 100° C., preferably from 55° C. to 90° C.

The membrane reactor is supplied with (meth)acrylic acid and alcohol. The acid/alcohol or alcohol/acid molar ratio refers to the contents of acid and of alcohol of all the streams supplying the membrane reactor. The process according to the invention may be carried out in the presence of a stoichiometric excess of alcohol, in the presence of a stoichiometric excess of acid, or under stoichiometric conditions of the reagents.

Advantageously, the process according to the invention is carried out under stoichiometric conditions of the reagents. In this mode of operation, it has been observed that the conversion is substantially equivalent to that obtained with a reaction conducted with an excess of acid or an excess of alcohol. In addition, due to the absence of a reagent in excess, the purification of the reaction medium is simplified with a lesser degree of recycling for the streams generated by the purification treatment. In particular, the energy consumption for recycling the unreacted alcohol is much lower.

Generally, it is suitable to guarantee a controlled stabilization of the reaction medium by adding, to the reactor, approximately from 200 to 2000 ppm of at least one polymerization inhibitor such as, for example, hydroquinone, hydroquinone methyl ether, di-tert-butyl-para-cresol (BHT), phenothiazine, para-phenylenediamine, TEMPO (2,2,6,6-tetramethyl-1-piperidinyloxy) or derivatives thereof, or di-tert-butylcatechol, activated by continuous injection of depleted air (7% $O_2$). Supplementary polymerization inhibitor is generally added at the subsequent purification treatment.

Figure 2:
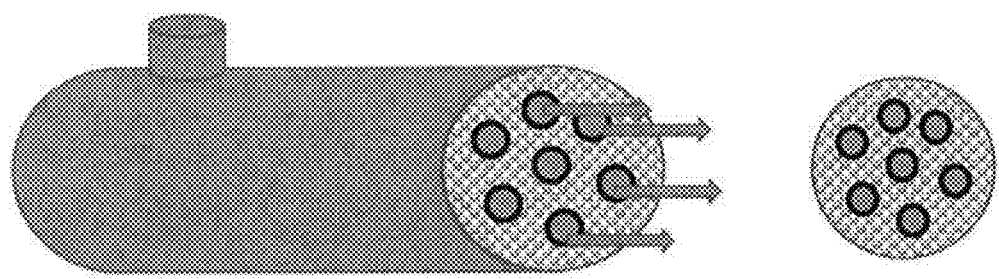
FIG. 2 schematically represents membrane reactors which may be used in the process according to the invention.
Figure 2:
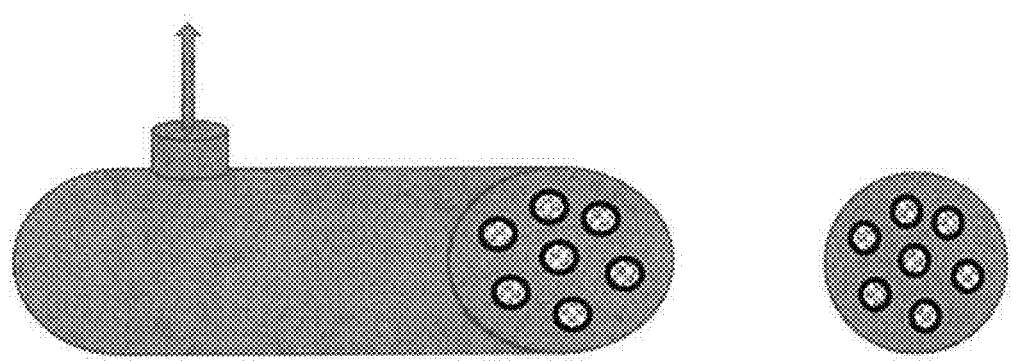

Examples of membrane reactors which may be used in the process according to the invention are illustrated in FIG. 1 and FIG. 2.

In FIG. 1 a) a tube can be seen consisting of a membrane, around which an esterification catalyst is located. The assembly is produced such that the permeate (separated water) leaves axially relative to the tube, with the retentate comprising the reaction medium with most of the water removed leaving the module radially.

In FIG. 1 b) a tube consisting of a membrane contains an esterification catalyst. According to this configuration, the assembly comprises a radial outlet for the permeate and the retentate leaves axially at the opposite end to the reagent supply.

FIG. 2 a) illustrates a membrane reactor of multitubular exchanger type comprising tubes according to the configuration of FIG. 1 a).

FIG. 2 b) corresponds to a multitubular exchanger in the configuration with radial outlet of the permeate. The water is eliminated through the tubes toward the shell which serves as body for this reactor. This shell is provided with tubing which enables it to be placed under vacuum. The water vapour extracted in this way from the reaction medium condenses outside of the shell via an external exchanger. The reaction medium is heated by an exchanger which pre-heats the supply.

Figure 3:
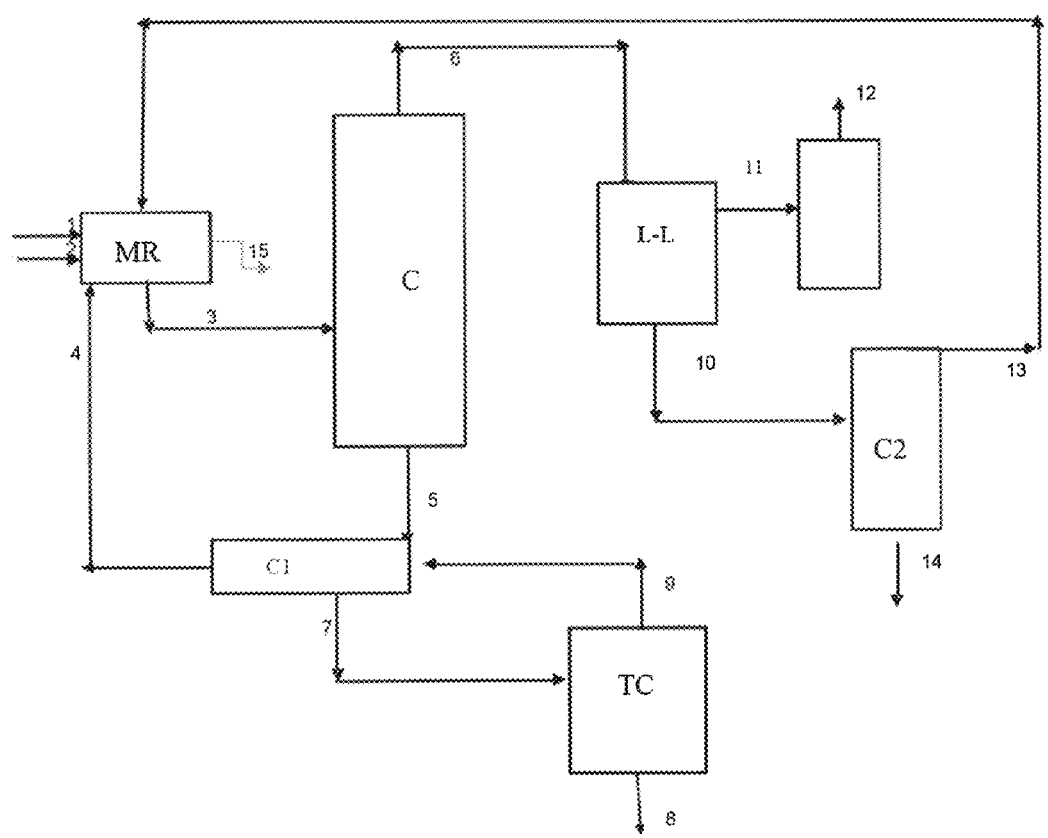
FIG. 3 schematically represents a facility for carrying out the process according to the invention, applied in particular to the synthesis of ethyl acrylate.

FIG. 3 represents a facility for producing alkyl (meth) acrylate according to the invention comprising a membrane reactor MR. This reactor MR is supplied by a pipe for conveying acid 1 and a pipe for conveying alcohol 2. The reactor preferentially contains an acid cation exchange resin-type catalyst contained in a tubular pervaporation module.

At the outlet of the membrane reactor, the reaction mixture 3 is sent to a distillation column C which separates, at the bottom, a stream 5 comprising essentially the unreacted acid, traces of light products (boiling point lower than that of the acid), and products having a boiling point higher than the acid, and at the top, a stream 6 comprising the ester formed and products lighter than the acid (unreacted alcohol, by-products such as ethyl acetate, acetic acid in the case of the synthesis of ethyl acrylate, for example).

The water eliminated through the wall of the membrane of the membrane reactor, stream 15, is condensed and sent (not shown in the diagram) into one of the purification columns to recycle any traces of organic compounds present, in particular the water which may be used for the liquid-liquid extraction phase.

The stream 5 from the bottom of column C is sent to a distillation column C1 which separates a stream 4 comprising the residual acrylic acid and lighter products, this stream 4 being recycled into the reactor MR. A stream 7 consisting essentially of heavy products (adducts) is separated from column C1 and subjected to thermal cracking in the thermal cracker TC.

The thermal cracking makes it possible to recycle the valuable products (starting compounds or finished product)

which can potentially be recovered from the heavy products fraction. The stream 9 of acid is recycled to the column C1, the stream 8 being incinerated.

The stream 6 from the top of the distillation column C is sent to a section for liquid-liquid extraction (settling tank or contactor) in order to generate, on the one hand, an aqueous phase 10 containing alcohol which is recycled to the reaction (stream 13) after distillation in a column C2 (the alcohol-depleted aqueous stream 14 possibly being recycled for the liquid-liquid extraction phase) and, on the other hand, an organic phase 11.

The organic phase 11 may be subjected to one or more supplementary steps of distillation in order to give the desired purified ester 12.

The process according to the invention makes it possible to make significant savings in terms of energy consumption of the facility.

The following examples illustrate the present invention without aiming to limit the scope of the invention as defined by the appended claims.

EXPERIMENTAL SECTION

The invention is illustrated with the reaction for synthesizing ethyl acrylate by esterification of acrylic acid with ethanol.

Example 1

The chemical equilibrium constant for the synthesis of ethyl acrylate is 2. Calculations of conversion at equilibrium were carried out for different conditions:

The reaction is conducted with an excess of alcohol (alcohol/acid molar ratio Rm=1.8).

The reaction is conducted with an excess of acid (acid/alcohol molar ratio=2.5, i.e. alcohol/acid molar ratio Rm=0.4).

The reaction is conducted under stoichiometric conditions (alcohol/acid molar ratio Rm=1).

The reaction is conducted in a conventional reactor R at a temperature of between 70 and 90° C.

The reaction is conducted in a membrane reactor MR at a temperature of between 70 and 90° C., and 80% of the water formed is eliminated from the reactor MR as it is formed.

The results are collated in Table 1 below.

TABLE 1

| | | | | | |
|---|---|---|---|---|---|
| Rm alcohol/acid | 1.8 | 1.8 | 1 | 0.4 | 0.5 |
| Type of reactor | R | MR | MR | R | MR |
| Conversion at equilibrium, % | 74 | 90 | 76 | 81 | 94 |
| Ester formed, mol | 0.74 | 0.9 | 0.76 | 0.81 | 0.94 |
| Residual alcohol, mol | 1.06 | 0.9 | 0.24 | 0.19 | 0.06 |
| Residual water, mol | 0.74 | 0.148 | 0.152 | 0.81 | 0.188 |
| Residual acid, mol | 0.26 | 0.1 | 0.24 | 1.69 | 1.56 |
| Residual alcohol, mol per mol of ester formed | 1.43 | 1 | 0.315 | 0.234 | 0.06 |
| Residual acid, mol per mol of ester formed | 0.35 | 0.09 | 0.315 | 2.09 | 1.66 |

It is observed that the conversion in a membrane reactor is higher than that in a conventional reactor, whether under conditions of excess alcohol or excess acid.

The membrane reactor operating under stoichiometric conditions leads to a substantially identical conversion to that obtained with a conventional reactor operating with an excess of alcohol or to that obtained with a conventional reactor operating with an excess of acid.

The membrane reactor according to the invention has this specific advantage of operating under conditions approaching stoichiometry, by leading to conversions comparable to those that exist for the conventional processes which require either an excess of alcohol or an excess of acid.

The result of this is that the residual amounts of alcohol and acid are lesser, which minimizes the energy loop for recycling the alcohol and reduces the risks of fouling linked to the residence time of the acrylic acid in the process.

Example 2

In an esterification reactor, the volume of esterification catalyst (or reaction volume) is determined as the product of the flow rate of reagents entering with the residence time in this reactor.

Mass per unit volume of the acid: 1000 kg/m$^3$,
Mass per unit volume of the alcohol: 800 kg/m$^3$ Considering a standard residence time of one hour in the reactor, for an ester production of 100 kg/h, the reaction volumes and the corresponding supply flow rates are determined from the data in Table 1.

TABLE 2

| | | | | | |
|---|---|---|---|---|---|
| Rm alcohol/acid | 1.8 | 1.8 | 1 | 0.4 | 0.4 |
| Type of reactor | R | MR | MR | R | MR |
| Supply flow rate, kg/h | 209 | 172 | 155 | 265 | 240 |
| Reaction volume, m$^3$ | 0.237 | 0.195 | 0.170 | 0.279 | 0.253 |

With an equivalent ester production, the membrane reactor operating under stoichiometric conditions makes it possible to minimize the volume of catalyst to be used.

Example 3

According to Example 2, a volume of 170 l of heterogeneous catalyst, for example of a resin of Amberlyst® type, makes it possible to produce 100 kg/h of ethyl acrylate corresponding to the simultaneous formation of approximately 18 kg/h of water.

A membrane reactor adapted to eliminate approximately 80% of the water generated, i.e. 14.4 kg/h of water, may be for example a membrane module comprising, according to a tubular exchanger configuration, 360 tubes of tubular membrane of HybSi® type, 25 mm in diameter and 1 m high, filled with catalyst, which corresponds to a surface area of approximately 8.5 m$^2$ for a membrane have a specific flow rate of aqueous permeate of 0.5 kg·m$^2$·h.

Example 4

An Aspen simulation was carried out for a unit for synthesizing ethyl acrylate EA comprising a membrane reactor eliminating 80% of the water formed during the reaction, and a purification assembly based on the use of a first distillation column C separating the residual acid, and a second column C2 separating the residual alcohol which is recycled to the reaction.

Table 3 below summarizes the energy data obtained in comparison with the energy data for an industrial ethyl acrylate unit.

It is observed that the separation of the water from the reaction generates an energy gain of the order of 25-35% over the 2 columns for recovery of the unreacted reagents.

TABLE 3

| | Conventional unit | Unit with membrane reactor | Gain, % |
|---|---|---|---|
| Reboiler column C, kcal/h | 4789947 | 3688259 | |
| Vapour 2.5 bar | 9.34 | 7.2 | 23% |
| EA entering column C, kg/h | 13496 | 13741 | |
| Kg vapour/kg EA | 0.69 | 0.52 | 24 |
| Reboiler column C2, kcal/h | 4317096 | 2886301 | |
| Vapour 2.5 bar | 8.42 | 5.63 | 33% |
| EA production, kg/h | 13496 | 13741 | |
| Kg vapour/kg EA produced | 0.62 | 0.41 | 34% |

The invention claimed is:

1. A process for producing an alkyl (meth)acrylate by direct esterification of (meth)acrylic acid with a linear or branched alcohol comprising from 1 to 10 carbon atoms, in the presence of an esterification catalyst, which employs a fixed bed membrane reactor in which the esterification reaction is conducted, while eliminating water generated by the reaction as water is formed, wherein the membrane reactor comprises a membrane module for dehydration coupled to a heterogeneous esterification catalyst, wherein the membrane module for dehydration is a pervaporation unit or a vapour permeation unit, and wherein the membrane module for dehydration is tubular, the esterification catalyst being located within the tubular membrane module for dehydration.

2. The process according to claim 1 chosen from the group consisting of continuous, semi-continuous, and batch type processes.

3. The process according to claim 1 wherein the membrane reactor comprises a hydrophilic membrane, or an inorganic membrane.

4. The process according to claim 1 wherein the membrane reactor comprises a membrane module for dehydration by pervaporation, based on modified silica.

5. The process according to claim 1 wherein the esterification reaction is conducted under stoichiometric conditions of the reagents.

6. The process according to claim 1 wherein the alcohol is selected from the group consisting of methanol, ethanol, butanol, 2-ethylhexanol and 2-octanol.

* * * * *